(12) United States Patent
Govil et al.

(10) Patent No.: US 9,327,061 B2
(45) Date of Patent: May 3, 2016

(54) POROUS BIOABSORBABLE IMPLANT

(75) Inventors: Amit Govil, Irvine, CA (US); Michael L. Jones, San Clemente, CA (US); Paul Lubock, Monarch Beach, CA (US)

(73) Assignee: SENORX, INC., Tempe, AZ (US)

( * ) Notice: Subject to any disclaimer, the term of this patent is extended or adjusted under 35 U.S.C. 154(b) by 1601 days.

(21) Appl. No.: 12/586,449

(22) Filed: Sep. 21, 2009

(65) Prior Publication Data

US 2010/0082102 A1    Apr. 1, 2010

Related U.S. Application Data

(60) Provisional application No. 61/192,896, filed on Sep. 23, 2008.

(51) Int. Cl.
*A61F 2/02* (2006.01)
*A61L 31/14* (2006.01)
(Continued)

(52) U.S. Cl.
CPC ............. *A61L 31/146* (2013.01); *A61F 2/0077* (2013.01); *A61F 2/02* (2013.01); *A61L 27/54* (2013.01); *A61L 27/56* (2013.01); *A61L 27/58* (2013.01); *A61L 31/148* (2013.01); *A61L 31/18* (2013.01); *A61L 2300/102* (2013.01); *A61L 2300/104* (2013.01); *A61L 2300/44* (2013.01)

(58) Field of Classification Search
CPC ..... A61L 31/146; A61L 27/58; A61L 31/148; A61L 27/54; A61L 27/56; A61L 31/18; A61L 2300/104; A61L 2300/44; A61L 2300/102; A61F 2/02; A61F 2/0077
USPC ............... 623/23.72, 23.75, 23.76, 23.73; 606/151, 214, 215; 424/424, 425, 426, 424/443, 444, 449
See application file for complete search history.

(56) References Cited

U.S. PATENT DOCUMENTS

| 2,192,270 A | 3/1940 | McGowan |
| 2,481,408 A | 9/1949 | Fuller et al. |

(Continued)

FOREIGN PATENT DOCUMENTS

| DE | 1029528 B | 5/1958 |
| EP | 0146699 A1 | 7/1985 |

(Continued)

OTHER PUBLICATIONS

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.

(Continued)

*Primary Examiner* — Ryan J Severson
*Assistant Examiner* — Rachel S Papeika

(57) ABSTRACT

The bioabsorbable implant described has a porous body formed of bioabsorbable materials that have an in vivo life span of at least 2 weeks, preferably at least three weeks and not greater than 20 weeks, preferably no greater than ten weeks. The implant has a scaffolding structure which facilitates tissue in-growth and ultimately tissue replacement of the scaffolding structure. The implant has a radiopaque imaging agent at least at the exterior margins and an orientation plurality of radiopaque elements in the interior of implant. The implant preferably has three radiopaque elements within the interior that form a plane within the implant interior.

1 Claim, 4 Drawing Sheets

(51) Int. Cl.
*A61F 2/00* (2006.01)
*A61L 27/54* (2006.01)
*A61L 27/56* (2006.01)
*A61L 27/58* (2006.01)
*A61L 31/18* (2006.01)

(56) References Cited

U.S. PATENT DOCUMENTS

| | | |
|---|---|---|
| 2,832,888 A | 4/1958 | Houston |
| 2,899,362 A | 8/1959 | Sieger, Jr. et al. |
| 2,907,327 A | 10/1959 | White |
| 3,341,417 A | 9/1967 | Sinaiko |
| 3,402,712 A | 9/1968 | Eisenhand |
| 3,516,412 A | 6/1970 | Ackerman |
| 3,593,343 A | 7/1971 | Viggers |
| 3,757,781 A | 9/1973 | Smart |
| 3,818,894 A | 6/1974 | Wichterle et al. |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,103,690 A | 8/1978 | Harris |
| 4,105,030 A | 8/1978 | Kercso |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,028 A | 2/1991 | Leonard et al. |
| 5,012,818 A | 5/1991 | Joishy |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,846 A | 3/1993 | Uno et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,613 A | 6/1994 | Houge et al. |
| 5,328,955 A | 7/1994 | Rhee et al. |
| 5,334,381 A | 8/1994 | Unger |
| 5,353,804 A | 10/1994 | Kornberg et al. |
| 5,354,623 A | 10/1994 | Hall |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A * | 7/1995 | Shaw ............................ 604/264 |
| 5,433,204 A | 7/1995 | Olson |
| 5,449,560 A | 9/1995 | Antheunis et al. |
| 5,451,406 A | 9/1995 | Lawin et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,667,767 A | 9/1997 | Greff et al. |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,747,060 A | 5/1998 | Sackler et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,775 A | 7/1998 | Milliman et al. |
| 5,795,308 A | 8/1998 | Russin |

(56) References Cited

U.S. PATENT DOCUMENTS

| | | |
|---|---|---|
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,830,178 A | 11/1998 | Jones et al. |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,142,955 A | 11/2000 | Farascioni et al. |
| 6,159,445 A | 12/2000 | Klaveness et al. |
| 6,161,034 A | 12/2000 | Burbank et al. |
| 6,162,192 A | 12/2000 | Cragg et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,200,258 B1 | 3/2001 | Slater et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,312,429 B1 | 11/2001 | Burbank et al. |
| 6,316,522 B1 | 11/2001 | Loomis et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 * | 4/2002 | Sirimanne et al. .................. 600/3 |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,424,857 B1 | 7/2002 | Henrichs et al. |
| 6,425,903 B1 | 7/2002 | Voegele |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,575,888 B2 | 6/2003 | Zamora et al. |
| 6,575,991 B1 | 6/2003 | Chesbrough et al. |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,628,982 B1 | 9/2003 | Thomas et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |

(56) References Cited

U.S. PATENT DOCUMENTS

| | | |
|---|---|---|
| 6,994,712 B1 | 2/2006 | Fisher et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,044,957 B2 | 5/2006 | Foerster et al. |
| 7,083,576 B2 | 8/2006 | Zarins et al. |
| 7,125,397 B2 | 10/2006 | Woehr et al. |
| 7,172,549 B2 | 2/2007 | Slater et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,569,065 B2 | 8/2009 | Chesbrough et al. |
| 7,577,473 B2 | 8/2009 | Davis et al. |
| 7,637,948 B2 | 12/2009 | Corbitt, Jr. |
| 7,651,505 B2 | 1/2010 | Lubock et al. |
| 7,819,820 B2 | 10/2010 | Field et al. |
| 2001/0006616 A1 | 7/2001 | Leavitt et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0193815 A1 | 12/2002 | Foerster et al. |
| 2002/0193867 A1 | 12/2002 | Gladdish, Jr. et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0236573 A1 | 12/2003 | Evans et al. |
| 2004/0001841 A1* | 1/2004 | Nagavarapu et al. ...... 424/178.1 |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236211 A1 | 11/2004 | Burbank et al. |
| 2004/0236212 A1 | 11/2004 | Jones et al. |
| 2004/0236213 A1 | 11/2004 | Jones et al. |
| 2005/0020916 A1 | 1/2005 | MacFarlane et al. |
| 2005/0033157 A1 | 2/2005 | Klein et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1* | 9/2005 | Allen et al. ............... 424/450 |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0036158 A1 | 2/2006 | Field et al. |
| 2006/0036159 A1 | 2/2006 | Sirimanne et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2006/0292690 A1* | 12/2006 | Liu et al. ............... 435/325 |
| 2007/0021642 A1 | 1/2007 | Lamoureux et al. |
| 2007/0038145 A1 | 2/2007 | Field |
| 2007/0057794 A1* | 3/2007 | Gisselberg et al. ........ 340/572.5 |
| 2007/0083132 A1 | 4/2007 | Sharrow |
| 2007/0087026 A1 | 4/2007 | Field |
| 2007/0106152 A1* | 5/2007 | Kantrowitz et al. .......... 600/424 |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0033280 A1 | 2/2008 | Lubock et al. |
| 2008/0039819 A1 | 2/2008 | Jones et al. |
| 2008/0097199 A1 | 4/2008 | Mullen |
| 2008/0114329 A1 | 5/2008 | Chernomorsky et al. |
| 2008/0188768 A1 | 8/2008 | Zarins et al. |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0030309 A1 | 1/2009 | Jones et al. |
| 2009/0069713 A1 | 3/2009 | Adams et al. |
| 2009/0076484 A1 | 3/2009 | Fukaya |
| 2009/0131825 A1 | 5/2009 | Burbank et al. |
| 2009/0171198 A1 | 7/2009 | Jones et al. |
| 2009/0216118 A1 | 8/2009 | Jones et al. |
| 2010/0010341 A1 | 1/2010 | Talpade et al. |
| 2010/0030072 A1 | 2/2010 | Casanova et al. |
| 2010/0030149 A1 | 2/2010 | Carr, Jr. |
| 2010/0121445 A1 | 5/2010 | Corbitt, Jr. |
| 2010/0204570 A1 | 8/2010 | Lubock |

(56) References Cited

U.S. PATENT DOCUMENTS

| | | |
|---|---|---|
| 2010/0331668 A1 | 12/2010 | Ranpura |
| 2011/0028836 A1 | 2/2011 | Ranpura |

FOREIGN PATENT DOCUMENTS

| | | |
|---|---|---|
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |
| EP | 1114618 A2 | 1/2001 |
| EP | 1152696 B1 | 11/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| GB | 708148 | 4/1954 |
| JP | 2131757 A | 5/1990 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9806346 A1 | 2/1998 |
| WO | 9908607 A1 | 2/1999 |
| WO | WO 99/35966 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | WO 00/54689 | 9/2000 |
| WO | 0108578 A1 | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | WO 2008/077081 | 6/2008 |

OTHER PUBLICATIONS

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N.E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large—Tissue Engineering", Biotechnol. Prog., vol. 14, No. 1, pp. 134-140, 1998.

Press release for Biopsys Ethicon Endo-Surgery (Europe) GmbH; The Mammotome Vacuum Biopsy System. From: http://www.medicine-news.com/articles/devices/mammotome.html. 3 pages.

Johnson & Johnson: Breast Biopsy (minimally invasive): Surgical Technique: Steps in the Mamotome Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

\* cited by examiner

POROUS BIOABSORBABLE IMPLANT

RELATED APPLICATION

This application relates to and claims priority from Provisional Application Ser. No. 61/192,896, filed on Sep. 23, 2008, which is incorporated herein in its entirety.

FIELD OF THE INVENTION

The invention is generally directed to porous bioabsorbable implants, for cavities in soft tissue such as in breast tissue after biopsy or lumpectomy procedures. Implants embodying features of the invention are particularly suitable for supporting such cavities and are imagable to facilitate conformal three dimensional irradiation.

BACKGROUND OF THE INVENTION

Biopsy and other tissue removal procedures in soft tissue can frequently lead to dimpling and other disfigurements unless a prostheses or implant is deployed within the cavity from which tissue has been removed. See for example U.S. Pat. No. 6,214,045, U.S. Pat. No. 6,638,308 and U.S. Pat. No. 6,881,226 (Corbitt et al.). Moreover, after tissue removing procedures involving cancer, such as lumpectomies, it is frequently desirable to irradiate the cavity lining to ensure effective treatment of any cancer cells that might remain.

While a number of implants have been proposed for filling body cavities after tissue removal procedures such as lumpectomies, few have met with significant commercial success.

SUMMARY OF THE INVENTION

The invention is generally directed to an implant for a body cavity which comprises a porous body formed of a bioabsorbable material having an in vivo life of at least two weeks but not more than twenty weeks, preferably at least three weeks but not more than about ten weeks. The implant has a porosity or is capable of forming a porosity so as to form temporary scaffolding within a body cavity from which tissue has been removed to ensure tissue in-growth into the cavity before significant bio-absorption of the implant. The implant is provided with a radiopaque imaging agent to ensure that at least the exterior margins are imagable such as by CT scans in order to formulate dosing programs. Additionally, the implant is provided with an interior orientation marker such as at least two and preferably three radiopaque elements within the body of the implant to facilitate orientation of the cavity and an exterior radiation source such as a linear accelerator for conformal irradiation of the tissue lining the cavity which is more likely to contain residual cancer cells. Externally energized orientation markers such as RFID's are also suitable. See for example U.S. Pat. No. 7,535,363 which is incorporated herein by reference.

The bioabsorbable material of the implant is at least in part a bioabsorbable chitosan or alginate. The body may also include a bioabsorbable material selected from the group consisting of dextran, starch, polylactic acid, polyglycolic acid and co polymers thereof, and gelatin, preferably cross-linked gelatin. The radiopaque imaging agent may be selected from the group of barium sulfate, barium carbonate, Silver Chloride, Silver Iodide, Silver Nitrate, Calcium Carbonate, Zinc Oxide and radiopaque metallic powder or particulate. The radiopaque imaging agent is in particulate and preferably powdered form so as to facilitate imaging, particularly the exterior margins of the implant. The plurality of marker elements for orientation that are placed within the body of the implant may be selected from Gold, Titanium, Platinum, Iridium, Tantalum, Tungsten, Silver, Rhenium and non-magnetic stainless steel. These metallic markers are incorporated into the implant to present a line (defined by two marker elements) and preferably a plane (defined by three marker elements) which allows an exterior radiation source, such as a linear accelerator, and the cavity to be aligned for effective irradiation of tissue lining the cavity.

The implant is sized and shaped so as to fit within the body cavity and to conform tissue lining the cavity about the implant. Generally, the implant will be spherical or oval in shape, although other shapes may be employed. It is preferred that the implant expand somewhat after deployment within the cavity, e.g. the implant materials swell (by taking up water or hydrating) upon contact with aqueous based fluids such as body fluids and other fluids which may be at the cavity site to ensure that tissue lining the cavity conform to the exterior of the implant. The final shape of the conformed tissue lining need not be the same shape as the original implant but the conformed shape of the tissue lining is simplified which eases dosage determinations and simplifies the irradiation patterns. Body cavities resulting from lumpectomy procedures, such as in a female's breast, can range from about 0.5 to about 8 cm, and are typically about 3 to about 6 cm, in maximum dimensions, so the implant should be approximately the same size and preferably slightly larger to ensure tissue conformance.

The implant is porous and has sufficient compressive strength to support breast tissue. The porosity should be sufficient to facilitate tissue ingrowth when deployed within the intracorporeal cavity. Porosity can have a pore size ranging from about 10 to about 600 micrometers. The surface pores are typically about 20 to about 80 micrometers and the interior pores are about 50 to about 200 micrometers. Implant porosity is preferably formed in the implant prior to deployment within the body cavity in order to control the size and shape of the implant. Porosity can be formed by removing fluids or dissolving soluble materials from a solidified body after its formation or by incorporating a gas or a gas forming agent in a mixture which forms the implant prior to the implant setting into its shape. Preferably, Another example might be freezing an aqueous solution of the chitosan or alginate in a mold to form a body then freeze dry the frozen body (preferably outside the mold) to remove the frozen aqueous fluid.

A variety of therapeutic or diagnostic agents may be incorporated into the implant including for example, hemostatic agents to form thrombus at the intracorporeal site, anesthetic agents to control pain, chemotherapeutic agents for treating residual neoplastic tissue or coloring agents to facilitate subsequent visual location of the site. Antibiotics, antifungal agents and antiviral agents may also be incorporated into the fibrous marker.

The implant can be formed by mixing about 0.5-4% (wt.) chitosan into an acidified (1-25% by weight acetic acid) aqueous solution along with about 0.5%-5% (wt.) powdered radiopaque imaging agent such as barium sulfate to facilitate the subsequent remote imaging of the implant. Up to 10% chitosan may be used, but the maximum solubility of chitosan is about 4.5% (wt.). The mixture can get quite viscous at the higher amounts of chitosan. The mixture is placed in a suitable mold which presents a desirable shape and the mixture is frozen at −1° to −196° C. for about 6-12 hours. The frozen body is removed from the mold and then placed in a lyophilizer (about 3 days) to remove water and to form a porous body. After freeze drying in the lyophilizer, the chitosan-containing body is neutralized using a base or buffer such as ammonium hydroxide (5-20% wt.), rinsed free of base or buffer with deionized water and then dried. The porous implant has the consistency of breast tissue.

In the case of an alginate, a soluble alginate such as sodium alginate is mixed into an aqueous solution along with a radiopaque agent as discussed above. The alginate-radiopaque agent mixture is poured into a suitable mold and then freeze dried or air dried to remove water to form the porous body. The porous body is removed from the mold and the soluble alginate is converted to a less soluble alginate by placing the porous body in a solution of calcium chloride which converts the sodium alginate to the less soluble calcium alginate. Gas bubbles may also be incorporated into the sodium alginate solution during mixing to provide porosity.

The plurality of radiopaque marker elements may be incorporated into the implant during its formation either as the solution solidifies in the mold or after the body has been formed. The plurality of marker elements should be placed inwardly from the exterior margin of the implant. Passageways may be formed in the porous body to desired locations for the radiopaque orientation elements.

The chitosan is preferably of high purity and high molecular weight. The degree of deacetylation is about 60 to 100% and preferably between 70 and 100%.

These and other advantages of the invention will become more apparent from the following detailed description of embodiments when taken in conjunction with the accompanying exemplary drawings.

DETAILED DESCRIPTION OF EMBODIMENTS OF THE INVENTION

Figure 1:
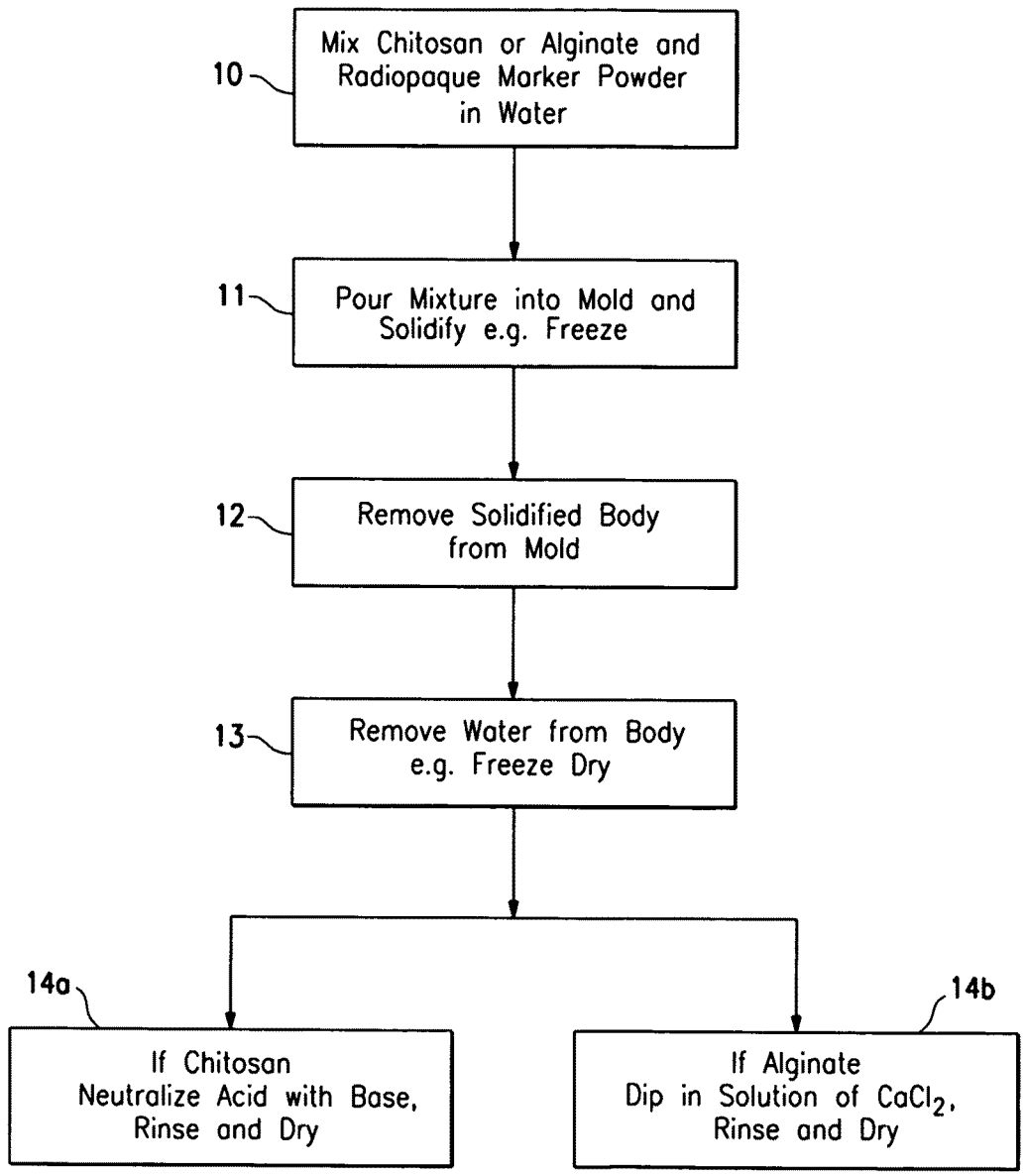
FIG. 1 is a flow chart that schematically illustrates a method for forming an implant embodying features of the present invention.

FIG. 1 is a flow chart that schematically illustrates a method for forming an implant which embodies features of the invention. Specifically, in the first step 10 a bioabsorbable material (chitosan or a soluble alginate) is mixed with water along with a powdered or particulate radiopaque imaging agent such as barium sulfate. A pore forming agent such as a gas may also be incorporated into the mixture. In second step 11, the mixture, which has to a certain extent gelled, is poured into a mold. The mold has a forming surface which puts the mixture into a desired shape where it solidifies or hardens to the point where it is self-supporting in the formed shape. In the illustrated case, the shape is spherical. In the third step 12, the formed body is removed from the mold and in step 13 water is removed from the body, preferably by freeze drying or air drying, to form a porous body. In the fourth step 14a, if the porous body is formed of chitosan, the residual acid in the body is neutralized with a suitable base such as ammonium hydroxide, rinsed and dried. In the fourth step 14b, if the porous body is formed of alginate, the porous body is dipped into a solution of $CaCl_2$, where at least part of the sodium alginate is converted to the less soluble calcium alginate, rinsed and dried. An orientation marker(s) may be inserted into the porous body by cannula or one or more passageways may be provided in the porous body so that the orientation marker(s) may be pushed to the desired location within body.

Figure 2:
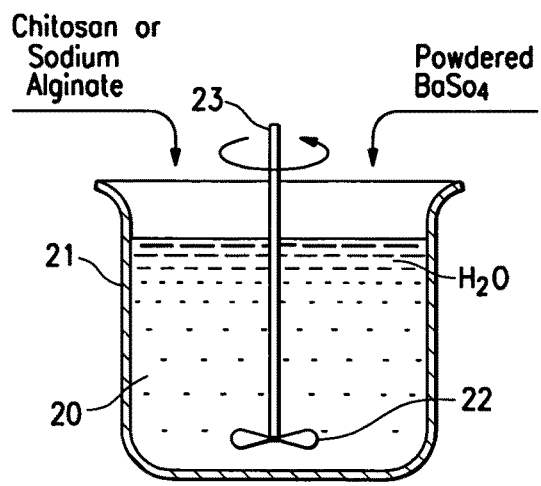
FIG. 2 is a schematic elevational view in section of a system for mixing components to make an implant embodying features of the invention.
Figure 4:
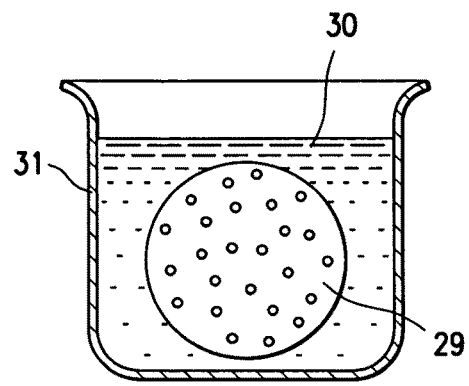
FIG. 4 is a schematic elevation view in section illustrating placing the dried porous body into a solution of $CaCl_2$ to convert the soluble alginate to a less soluble alginate.
Figure 3:
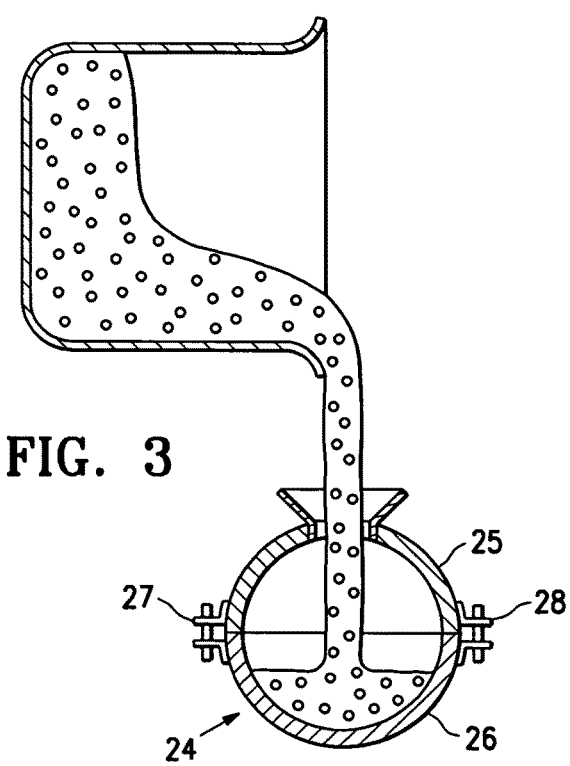
FIG. 3 is a schematic elevational view in section illustrating pouring the mixture into a mold to form the implant.
Figure 5:
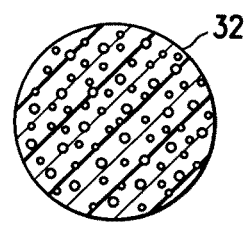
FIG. 5 is a transverse cross-sectional view of an implant after treating in the solution of $CaCl_2$.

FIG. 2 illustrates adding the bioabsorbable chitosan or sodium alginate and barium sulfate powder to a body of water 20 contained in a suitable container 21. The water 20 is mixed with the mixing element or propeller 22 attached to rotating shaft 23. Bubbles can be whipped into the mass or other pore forming agents can be introduced into the body of water 20. Additionally, water soluble materials can be added so that they may subsequently be dissolved away after the body has been dried. As shown in FIG. 3, the body of fluid or gel is then poured into a spherical mold 24 which has an upper half 25 and a lower half 26 that are interconnected by brackets 27 and 28. After the body has set, water is removed, e.g. by freeze drying, so as to form a porous spherical body 29. If the body contains chitosan, the body is treated with a base to neutralize the residual acid. If the body contains sodium alginate, then as shown in FIG. 4, the porous spherical body 29 is introduced into an aqueous $CaCl_2$ solution 30 in container 31 where at least part of the sodium alginate is converted to calcium alginate that quickly precipitates. A transverse section of the final implant 32 is schematically illustrated in FIG. 5.

Figure 6:
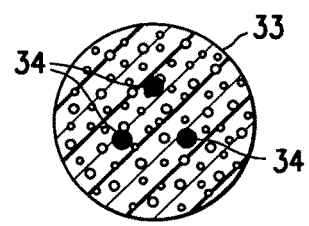
FIG. 6 is a transverse of an implant embodying features of the invention having an orientation marker with three radiopaque elements.

FIG. 6 is a transverse cross-section of an implant 33 which has three imagable radiopaque elements 34 (e.g. gold particles) situated within the interior of the implant and spaced inwardly from the outer surface. The three radiopaque elements (e.g. imagable gold particles) are shown at the apices of an equilateral triangle which can be used as a guide for the relative positioning between the patient's breast and a linear accelerator to provide effective irradiation of tissue surrounding the lumpectomy cavity in the patient's breast. Minimally, there should be two radiopaque elements to define a line and preferably three to define a plane. However, there may be more but they should be on the same plane. The radiopaque imaging agent (barium sulfate) in the implant enables the exterior margins of the implant to be imaged in a CT scan and this facilitates determining an appropriate irradiation dosage plan for the linear accelerator to ensure effective treatment of any residual cancer cells remaining in the cavity lining after the lumpectomy.

Example I

Figure 7:
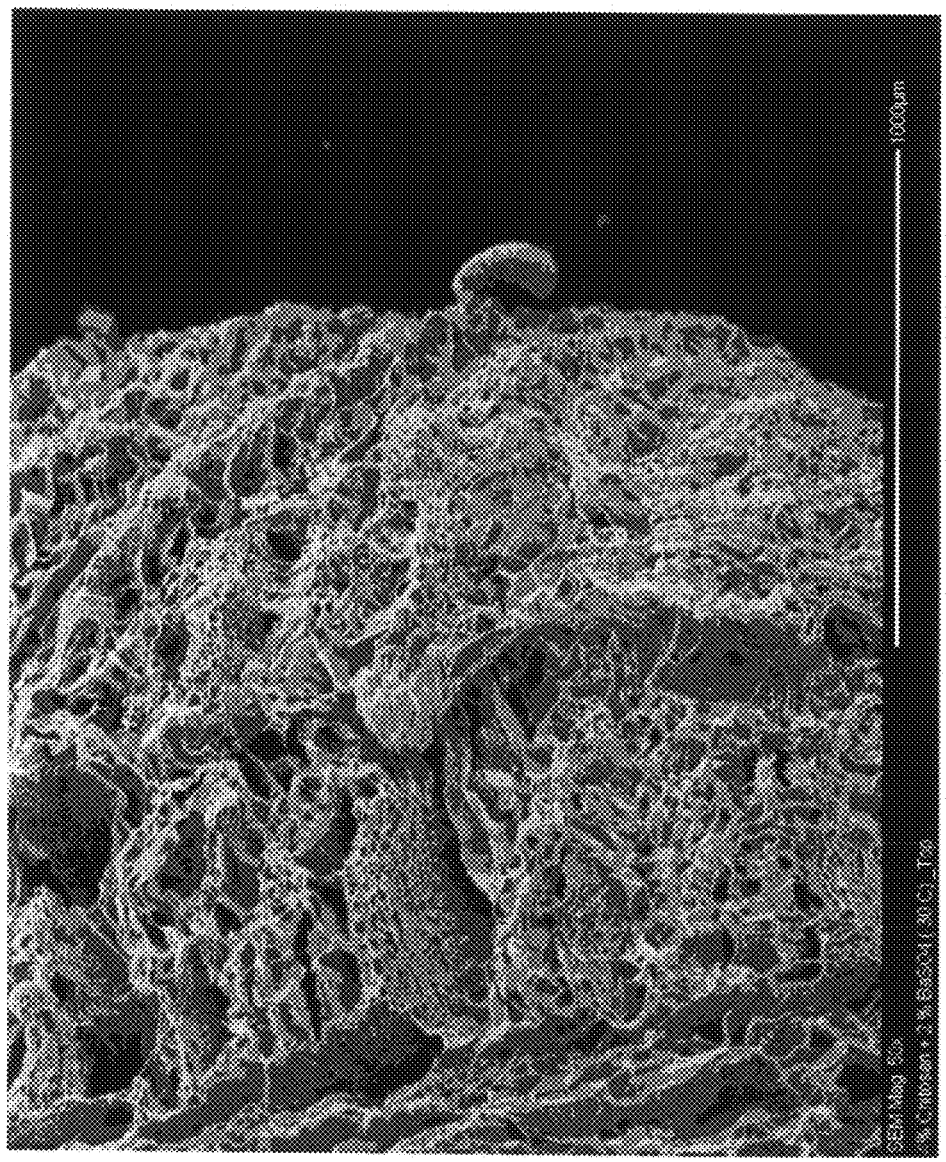
FIG. 7 is a scanning electron micrograph (30×) of a sectional view of an implant embodying features of the invention taken near the surface of the implant.
Figure 8:
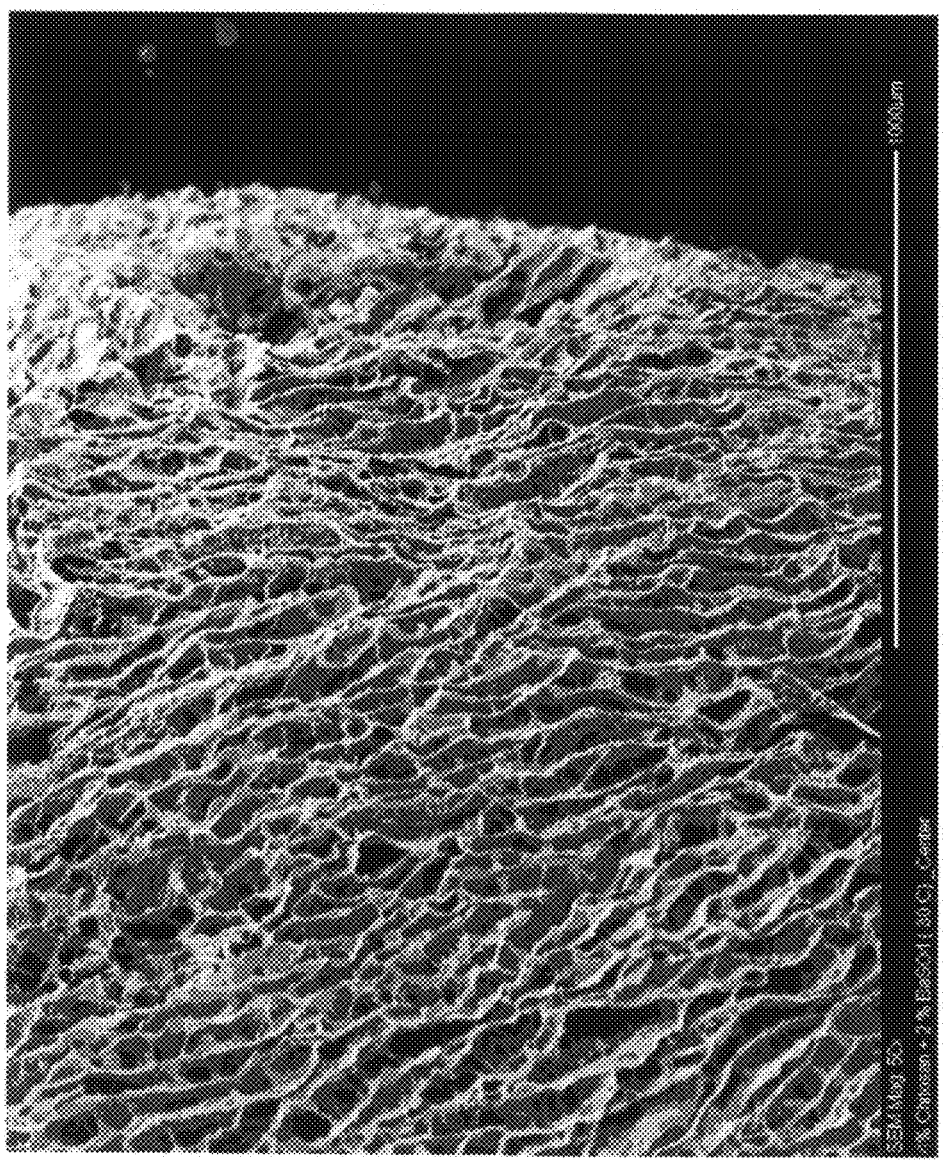
FIG. 8 is a scanning electron micrograph (30×) of a sectional view of an implant embodying features of the invention taken in the interior of the implant.

An acidic aqueous solution (12.5% acetic acid) was prepared containing 4% by weight chitosan and 2% by weight barium sulfate. The solution was placed in a spherical mold and was then frozen in the mold at −30° C. for 16 hours. The frozen body was removed from the mold and lyophilized for 3 days to remove water. The lyophilized body was neutralized in a 10% solution of ammonium hydroxide for one hour and then rinsed free of the ammonium hydroxide with deionized water. The body was vacuum dried for 16 hours. The body had the spongy consistency approximating breast tissue and had sufficient compressive strength to support breast tissue surrounding a lumpectomy cavity. It comprised 67% chitosan and 33% barium sulfate. An SEM micrograph (30×) of the surface porosity is shown in FIG. 7 and an SEM micrograph (30×) of the central porosity is shown in FIG. 8. The implant had the spongy consistency approximating breast tissue. The implant could be made harder by increasing the amount of chitosan.

Example II

A quantity of sodium alginate (0.5 to about 4% (wt.)) is dissolved in water to form a paste, viscous fluid or gel and air or other biocompatible gas is introduced into the mixture. The mixture is placed in a mold of a desired implant shape and then freeze dried or air dried in the desired shape. The formed implant structure of sodium alginate is introduced into a solution of calcium chloride (0.5 to about 4% (wt.)) where at least part of the sodium alginate is converted to calcium alginate which precipitates. The precipitated porous structure of the implant is introduced into a body cavity from which tissue has been removed. The implant remains at the site for sufficient period of time so as to act as scaffolding to facilitate tissue in-growth within the body cavity. Starch, such as corn starch in finely divided particulate form, can be incorporated into the sodium alginate-water mixture so that when the calcium alginate is formed, it precipitates about the starch particles to minimize shrinkage during the conversion of sodium alginate to calcium alginate. The starch degrades quickly within the body cavity in the presence of body fluid. The alginate on the surface of the implant degrades to open up the incorporated starch particles to degradation which provides an evolving porosity. The weight ratio of starch to alginate can range from about 15:1 to about 1:1.

Example III

This example is similar to Example II except 30 grams of salt (NaCl) granules are mixed with about 30 ml of 3% (wt.) sodium alginate aqueous solution. The solution placed in a spherical mold and then is frozen for 4 hours. The frozen implant was removed from the mold and placed in a 2% (wt.) calcium chloride solution, forming calcium alginate gel and dissolving at least some of the incorporated salt granules to form a porous structure. The implant had the spongy consistency approximating breast tissue. The implant could be made harder by increasing the amount of sodium alginate in solution, decreasing the amount of salt or decreasing the size of the salt granules.

While one or more particular forms of the invention have been illustrated and described herein in the context of an implant, particularly a breast implant for use after a lumpectomy, it will be apparent that the implant having features of the invention may find use in a variety of locations and in a variety of applications where tissue has been removed. Moreover, various modifications can be made without departing from the spirit and scope of the invention. Accordingly, it is not intended that the invention be limited to the specific embodiments illustrated. It is therefore intended that this invention to be defined by the scope of the appended claims as broadly as the prior art will permit, and in view of the specification, if need be. Moreover, those skilled in the art will recognize that features shown in one embodiment may be utilized in other embodiments.

Terms such as "element", "member", "device", "section", "portion", "step", "means" and words of similar import when used in the following claims shall not be construed as invoking the provisions of 35 U.S.C. §112(6) unless the following claims expressly use the term "means" followed by a particular function without specific structure or expressly use the term "step" followed by a particular function without specific action. All patents and patent applications referred to above are hereby incorporated by reference in their entirety.

What is claimed is:

1. An implant for a body cavity, comprising a body formed of a bioabsorbable material having a porosity sufficient to ensure tissue in-growth before significant bio-absorption of the implant, a radiopaque imaging agent which facilitates imaging of exterior margins of the implant and an interior orientation marker comprised of a plurality of radiopaque elements spaced inwardly from the exterior margins of the implant to facilitate relative orientation between the implant and a radiation source, wherein the plurality of radiopaque elements include at least three radiopaque elements arranged to form a plane within the interior of the implant wherein the plurality of radiopaque elements consists of three radiopaque elements which are located at apices of an equilateral triangle within the interior of the implant to form the plane.

\* \* \* \* \*